United States Patent
McMillan

(10) Patent No.: US 7,294,466 B2
(45) Date of Patent: Nov. 13, 2007

(54) MULTIPLEXED DETECTION OF BIOLOGICAL AGENTS

(75) Inventor: William A McMillan, Cupertino, CA (US)

(73) Assignee: Cepheid, Sunnyvale, CA (US)

( * ) Notice: Subject to any disclaimer, the term of this patent is extended or adjusted under 35 U.S.C. 154(b) by 0 days.

(21) Appl. No.: 11/123,363

(22) Filed: May 6, 2005

(65) Prior Publication Data

US 2005/0250146 A1 Nov. 10, 2005

Related U.S. Application Data

(60) Provisional application No. 60/569,209, filed on May 7, 2004.

(51) Int. Cl.
*C12Q 1/68* (2006.01)
*G01N 33/53* (2006.01)
*C12N 15/11* (2006.01)
*G06F 19/00* (2006.01)

(52) U.S. Cl. .................. 435/6; 435/7.1; 536/24.3; 702/19

(58) Field of Classification Search ............. None
See application file for complete search history.

(56) References Cited

U.S. PATENT DOCUMENTS 6,458,535 B1 * 10/2002 Hall et al. ............. 435/6

OTHER PUBLICATIONS

Zhang et al, J. Mol. Biol. 317: 225 (2002).*
Molecular Biology Reagents/Protocols 1992, United States Biochemical Corporation, 1991, Cleveland, Ohio, pp. 218-219.*
PCT International Search Report and Written Opinion, PCT/US05/16257, Nov. 29, 2006, 7 pages.

* cited by examiner

*Primary Examiner*—James Martinell
(74) *Attorney, Agent, or Firm*—Fenwick & West LLP

(57) ABSTRACT

Described are methods, kits and systems for multiplexed detection of biological agents in a sample, e.g., multiplexed detection of e.g., bacteria, viruses, and biological toxins. The method utilizes two markers for each agent; the presence or absence in a sample of each of the two markers per agent is determined in separate reactions; however each reaction is used to detect a single marker for multiple agents. Also disclosed is the multiplexed detection method using real time PCR. The invention provides an efficient, cost-effective, and specific method for multiplexed detection of biological agents.

35 Claims, 4 Drawing Sheets

MULTIPLEXED DETECTION OF BIOLOGICAL AGENTS

CROSS REFERENCE TO RELATED APPLICATIONS

This application claims the benefit of U.S. Provisional Application No. 60/569,209, filed May 7, 2004, the entire disclosure of which is hereby incorporated by reference in its entirety for all purposes.

STATEMENT REGARDING FEDERALLY SPONSORED RESEARCH OR DEVELOPMENT

Not applicable.

BACKGROUND OF THE INVENTION

1. Field of the Invention

The invention relates to methods, kits, and systems for detection of a plurality biological agents in a sample utilizing a minimal number of containers, useful for diagnostic assays and screening for disease agents.

2. Description of the Related Art

Diagnostic assays that sensitively, specifically, and quickly detect biological agents, e.g., pathogens, in samples are becoming increasingly important for both disease and diagnostic bioagent monitoring. Few assays are able to accurately detect physiologically or clinically relevant organisms on an appropriate time-scale for the early detection of the presence of an infective or otherwise harmful agent. To date, the most sensitive detection methods involve PCR. Determining the presence or absence of a plurality of biological agents in a single sample can be performed using multiplexed detection methods. Multiplexed real time PCR is one method that can be used for this type of diagnostic assay.

Assays based on PCR can be limited by the complexity of optimizing the PCR reactions to test for multiple agents in a cost-effective number of reaction tubes. As a general rule, the number of probes needed to support a highly specific confirmation result range from two to as many as six sequences. As one of skill in the art will be aware, optimizing a PCR reaction with many different primer pairs and probes can be a formidable task that becomes increasingly unmanageable as the number of agents to be detected increases.

Assays based on PCR can also be limited by the number of unique chemical labels available for analysis of results. For example, real time PCR assays generally employ fluorescent labels. When performing multiplexed real time PCR, the number of labels that can be used in a single reaction is limited by the number of fluorescent color channels available in the optical detection system used.

An attractive approach to overcome these and other limitations of current multiplex assays is provided by the present invention.

SUMMARY OF THE INVENTION

Disclosed herein are methods for efficient, cost-effective, and specific multiplexed detection of multiple biological agents in a sample, e.g., multiplexed detection of biological agents; e.g., bacteria, viruses, biological toxins, and the like. The method utilizes two markers for each agent; the presence or absence of each of the two markers per agent is determined in separate containers. Each container is used to detect a single marker for multiple agents. If no markers for any agent are detected in the first container, the second container does not need to be utilized, saving significant time and money. In a preferred embodiment, multiplexed fluorescent real time PCR is used to determine the presence or absence of up to nine different biological agents in a sample using only two sets of reactions. Kits and systems employing the method are also disclosed.

According to one aspect, the invention provides a method for detecting at least first and second biological agents, the first agent having first and second markers, and the second agent having third and fourth markers, the method comprising the steps of preparing first and second mixtures from at least one sample suspected of containing the agents; detecting the presence or absence of the first and third markers in the first mixture in a first container; and detecting the presence or absence of the second and fourth markers in the second mixture in a second container; whereby the presence of the first and second markers indicates the presence of the first biological agent in the sample, and the presence of the third and fourth markers indicates the presence of the second biological agent in the sample. Biological agents that can be identified using the method of the invention include bacteria cells, virus particles and biological toxins. Markers that can be detected include nucleic acids, proteins and polysaccharides. Markers can be detected in mixtures including, e.g., solutions, suspensions, emulsions or powders.

According to another aspect, the present invention provides a method for optically detecting the presence or absence of a number of biological agents greater than the number of color channels used to detect the presence or absence of the agents. Each of the biological agents has respective first and second nucleic acid sequences that differentiate the biological agent from the other biological agents. The method comprising the step of forming first and second mixtures in first and second containers, respectively, from at least one sample suspected of containing the agents. The first mixture contains, for each of the biological agents, a respective first probe set for labeling the first nucleic acid sequence of the biological agent. The second mixture contains, for each of the biological agents, a respective second probe set for labeling the second nucleic acid sequence of the biological agent. At least two of the first probe sets in the first mixture have the same emission wavelength ranges to be detected in the same color channel, and the at least two corresponding second probe sets in the second mixture have different emission wavelength ranges to be detected in different color channels. The method further comprises the steps of optically reading the presence or absence of probe signals from the at least two of the first probe sets in the first mixture have the same emission wavelength ranges; optically reading the presence or absence of probe signals from the at least two corresponding second probe sets in the second mixture have different emission wavelength ranges; and determining from the combination of probe signals received from each of the mixtures the presence or absence of the biological agents.

According to another aspect, the invention provides a method for detecting at least first and second biological agents, the first agent comprising first and second markers, and the second agent comprising third and fourth markers. The method comprises the steps of preparing a first mixture in a first container from at least one sample suspected of containing the agents and detecting the presence or absence of the first and third markers in the first container. If either of the first or third markers is present in the first container, then a second mixture is prepared in a second container from the at least one sample and the presence or absence of the second and fourth markers in the second container is detected. The presence of the first and second markers indicates the presence of the first biological agent in the sample, and the presence of the third and fourth markers indicates the presence of the second biological agent in the sample.

According to another aspect, the invention provides a kit for detecting at least first and second biological agents, the first agent comprising first and second markers, and the second agent comprising third and fourth markers. The kit comprises at least first and second containers. The first container houses a first probe specifically recognizing the first marker and a second probe specifically recognizing the third marker. The second container houses a third probe specifically recognizing the second marker and a fourth probe specifically recognizing the fourth marker. In some embodiments, each of the probes has a detectable label, the detectable label of the first probe is the same as the detectable label of the third probe, and the detectable label of the second probe is different from the detective label of the fourth probe. In some embodiments, each of the probes has a fluorescent label, the fluorescent labels of the first and second probes have respective emission maxima wavelengths within 100 nm of each other, and the third and fourth probes have respective emission maxima wavelengths that differ by more than 100 nm. In other embodiments, at least the first probe is a nucleic acid probe, and at least the fourth probe is an antibody. In some embodiments, the first, second, third, and fourth markers comprise first, second, third, and fourth nucleic acid sequences, respectively, and the probes comprise hybridization probes for labeling the nucleic acid sequences. In some embodiments, the first container further contains amplification reagents including primers for amplifying the first and third nucleic acid sequences, and the second container further contains amplification reagents including primers for amplifying the second and fourth nucleic acid sequences.

According to another aspect, the invention provides a system for detecting at least first and second biological agents. The first agent comprises first and second markers, and the second agent comprises third and fourth markers. The system comprises at least first and second containers, the first container housing reagents for detecting the first and third markers and the second container housing reagents for detecting the second and fourth markers. The system also comprises at least one detector arranged to detect the presence or absence of the markers in the containers. The system further comprises at least one controller (e.g., a computer or microprocessor) in communication with the at least one detector. The controller is programmed with computer-readable instructions to perform a series of operations comprising initiating a detection reaction in the first container, receiving data from the detector, and determining from the data the presence or absence of the first and third markers in the first container. If the first or third marker is present in the first container, then the controller performs a second series of operations comprising initiating a second detection reaction in the second container, receiving additional data from the detector, and determining from the additional data the presence or absence of the second or fourth markers in the second container. The presence of the first and second markers indicates the presence of the first biological agent in a sample, and the presence of the third and fourth markers indicates the presence of the second biological agent in the sample. In some embodiments, the first, second, third, and fourth markers comprise first, second, third, and fourth nucleic acid sequences, and the first and second containers comprise cartridges for extracting nucleic acid from a sample and for holding the nucleic acid for detection.

According to another aspect, the invention provides an automated system for determining the presence or absence of a plurality of agents, each of the agents comprising respective first and second nucleic acid sequences that differentiate the agent from the other agents. The automated system comprises at least one temperature control system for subjecting first and second reaction mixtures suspected of containing the agents to nucleic acid amplification conditions. The first reaction mixture contains reagents and probes for amplifying and detecting the first nucleic acid sequence of each of the agents, and the second reaction mixture contains reagents and probes for amplifying and detecting the second nucleic acid sequence of each of the agents. At least one detection mechanism is arranged to detect probe signals from the reaction mixtures. The automated system further comprises at least one controller (e.g., computer or microprocessor) in communication with the at least one temperature control system and with the at least one detection mechanism. The controller is programmed to perform the steps of sending control signals to the temperature control system to subject the first reaction mixture to nucleic acid amplification conditions, and determining from probe signals received from the first reaction mixture if the first nucleic acid sequence of any of the agents is present in the first reaction mixture. If the first nucleic acid sequence of any of the agents is present in the first reaction mixture, then the controller sends control signals to the temperature control system to subject the second reaction mixture to nucleic acid amplification conditions. The controller is further programmed to determine from probe signals received from the second reaction mixture if the second nucleic acid sequence of any of the agents is present in the second reaction mixture. The presence of the first and the second nucleic acid sequences of any of the agents is indicative of the presence of that agent.

DETAILED DESCRIPTION OF THE INVENTION

Figure 1:
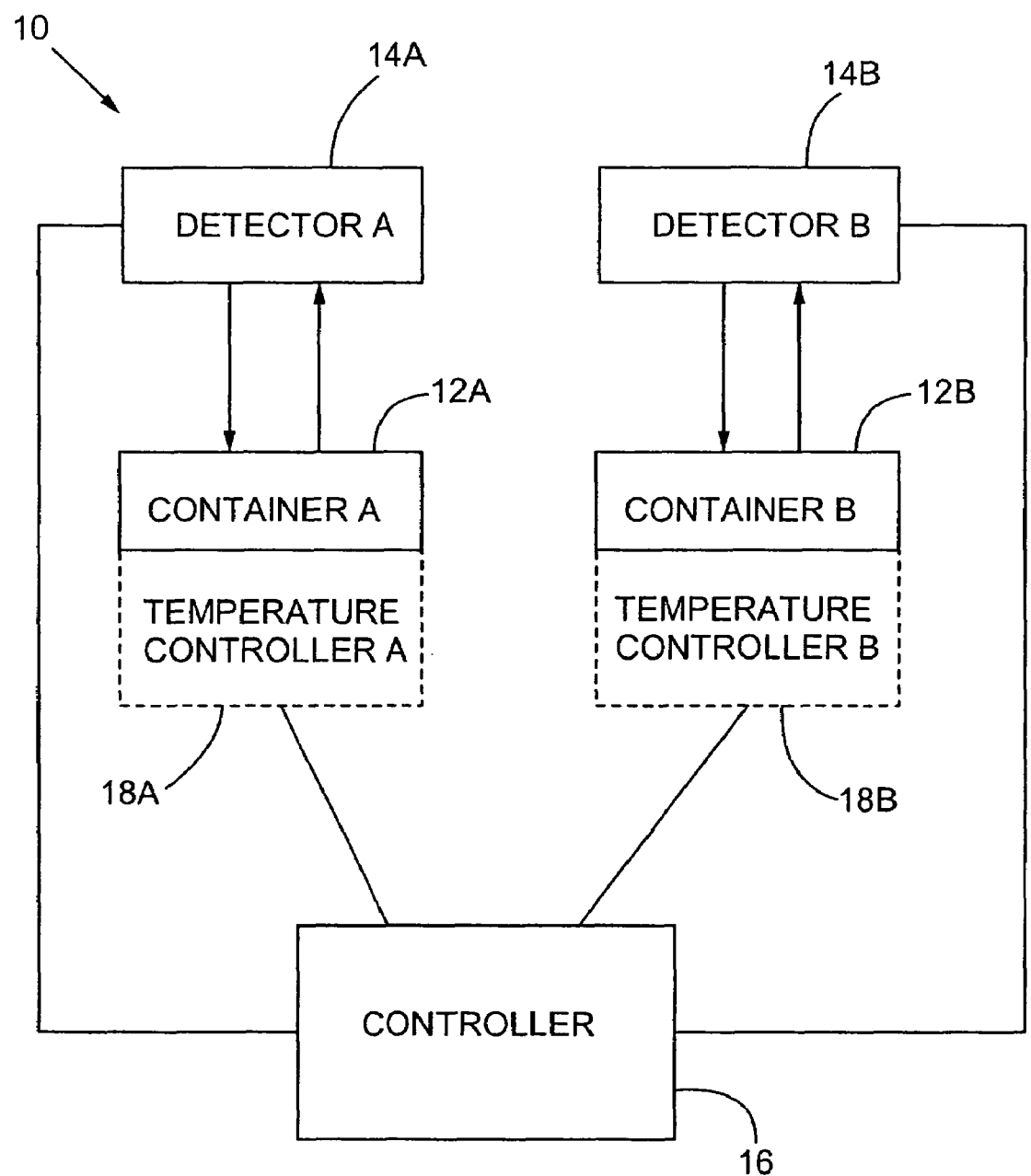
FIG. 1 shows a schematic block diagram of a system for detecting at least first and second biological agents according to an embodiment of the invention.

Briefly, and as described in more detail below, described herein are methods, kits, and systems for efficient, cost-effective, and specific multiplexed detection of multiple agents, e.g., methods for highly multiplexed real time PCR detection of biological agents, e.g., bacteria, viruses, biological toxins, and the like.

Several features of the current approach should be noted. The method uses as few as two markers for each biological agent, e.g., two probes are used to detect two gene sequences (markers) for each bacterial strain. The presence or absence of each of the two markers per agent is determined in separate containers, e.g., detection of the two different gene sequences is performed in separate real time PCR reactions. Each container is used to detect a single marker for multiple agents; because of the binary feature of the analysis, e.g., two different probes in two different containers (reactions), multiple probes in the same container can comprise the same label. If no markers for any agent are detected in the first container, the second container does not need to be utilized.

Advantages of this approach are numerous. The method overcomes the difficulties and complexities of optimizing a detection reaction with multiple probes for a single agent, e.g., optimizing a single PCR reaction with multiple probes directed to a single bacterial nucleic acid. This is the result of using a method that separates the two probes for each agent into two separate containers, e.g., two separate reactions.

In addition, the method overcomes the limitation on the number of agents that can be detected in a single container imposed by a defined number of labels that can be detected in a single container. For example, real time PCR using a standard fluorescent detection system includes 4 different fluorescent channels. This generally leads to an increase in the number of containers that must be used when doing multiplexed reactions. Since the method of the invention separates the two probes for each agent into separate containers, each label that is detected can be used with multiple probes, with an analysis of the results from both containers providing the identification (present or not) of the agent. The method is also cost-efficient when faced with a limited number of detection options per container, e.g., a limited number of fluorescent channels.

The invention is useful for specific, efficient, cost-effective detection of multiple agents in a sample. The methods can be employed in diagnostic assays that sensitively, specifically, and quickly detect agents in samples. The types of agents that can be detected include, e.g., bacteria, viruses, and toxins. For example, the methods of the invention are useful in diagnostic assays for disease pathogens.

Definitions

Terms used in the claims and specification are defined as set forth below unless otherwise specified. It must be noted that, as used in the specification and the appended claims, the singular forms "a," "an" and "the" include plural referents unless the context clearly dictates otherwise.

Abbreviations used in this application include the following:

"PCR" refers to polymerase chain reaction.

"Biological agent" refers to any biological material that is to be identified, and includes, e.g., cells, viruses, naturally occurring proteins, glycoproteins, complex and simple sugars, nucleic acids, lipids and lipoproteins. "Biological agent" also refers to toxins, particularly nucleic acid and protein-based toxins, both natural and synthetic.

"Color channel" refers to a detection wavelength range.

"Detectable label" refers to any composition that is capable of producing, either directly or indirectly, a signal detectable by spectroscopic, radioisotopic, photochemical, biochemical, immunochemical, electrical, optical or chemical means. Examples include but are not limited to isotopic labels, immune labels, and colored or fluorescent dyes.

"Detecting" refers to determining the presence or absence of a marker in a sample. Detecting also refers to determining the presence or absence of a biological agent in a sample, based on the analysis of detecting markers.

"Emission maxima" refers to the wavelength at which a previously excited fluorescent label subsequently releases the greatest energy, in the form of light.

"Absorbance maxima" refers to the wavelength at which a fluorescent label absorbs the maximum amount of energy in the form of photons.

"Marker" refers to a macromolecular, microscopic or molecular characteristic of a biological agent that distinctively identifies the biological agent.

Methods of the Invention

The invention provides methods wherein identification of multiple biological agents is determined, e.g., the presence or absence is determined, in a multiplex manner. The method overcomes difficulties of optimizing detection of multiple markers for a single biological agent. The method is also designed in a cost efficient manner to utilize a minimal number of containers. Each container comprises means to detect multiple markers for multiple agents; however, each container comprises means to detect only a single marker unique to each agent. Analysis of the results from a single container (if the results are completely negative) or all containers provides the desired result of identification (presence or absence) of the multiple biological agents. In general, markers are detected using a probe, e.g., an oligonucleotide that hybridizes to an amplified gene sequence. The probe is labeled for detection, e.g., fluorescently labeled.

The maximum number of biological agents, X, that can be detected in sample using the methods of the invention is only limited by the number of different probe labels, PL, that can be differentially detected in a single container, the number of containers to be used (N) and the number of internal controls (IC). The maximum number of biological agents that can be identified, X, using two containers is defined by the following: $X = (PL - IC)^N$.

For example, in one embodiment, methods of the invention can be performed using real time PCR for detection of gene sequences (markers) to determine the presence or absence of specific bacterial cells (biological agents) in a sample. In one embodiment, real time PCR is performed using the Cepheid I-CORE® system. This system utilizes four optical color channels (PL=4). In one embodiment, a single internal control is used in each container (IC=1). Using this system, a maximum of 9 different biological agents can be identified in a sample using only two containers. In another embodiment, two internal controls (IC=2) are used in each container, and a maximum of 4 different biological agents can be identified using two containers.

As the number of probe labels that can be differentially detected increases, the number of agents that can be identified increase without increasing the number of container used. The following table illustrates the maximum number of agents that can be identified using the methods of the invention based on the number of PL and ICs and 2 containers.

| 4 probe labels | | 5 probe labels | | 6 probe labels | |
| --- | --- | --- | --- | --- | --- |
| # IC's | # agents | # IC's | # agents | # IC's | # agents |
| 1 | 9 | 1 | 16 | 1 | 25 |
| 2 | 4 | 2 | 9 | 2 | 16 |
|   |   | 3 | 4 | 3 | 9 |
|   |   |   |   | 4 | 4 |

Illustrative of the improvement of the invention over the prior art is as follows. A method of detection that uses four detectable labels enables the detection of four separate markers in a single reaction. In the case where more than one marker per agent needs to be measured and reserving at least one detectable label for an internal control (IC), fewer than four agents; e.g., at most one agent, can be detected in a single reaction. In addition, difficulties arise when attempting to detect multiple markers for a single biological agent in a single reaction. However, using the method of the invention, it is possible to identify more than 4 agents, even when more than one marker is required for their accurate identification. Indeed, many agents may be detected depending on how many probes share a detectable label.

In one embodiment, the number of agents that can be detected with two containers is expanded by labelling more than one probe in a single container with the same detectable label and offsetting the detectable label assignments between the two containers. Analysis of the result from two containers provides identification of the biological agent present in the sample.

In another embodiment of the invention, analysis of the two containers is performed sequentially. If no markers are detected in the first container, indicating that no agents are present in the sample, the second container is not utilized.

The following models of the method of the invention more clearly illustrate the method of the invention. The models include number of agents to be identified, the system for labeling probes, and the expected results. Although the models are presented with the embodiment of gene sequence markers detected using fluorescent real time PCR, one of skill in the art will readily appreciate that other markers, probes, and methods of detection can be used within the same method.

Model for Identification of 3 Agents Using 4 Detectable Labels

In this embodiment, the method is used to screen for and identify three agents, e.g., organisms. Each organism can be identified by two markers, e.g., gene sequences. The markers are detected by probes having a detectable label, e.g., fluorescently labeled probes. Presence or absence of a gene sequence in a sample is performed using real time PCR and a four channel Cepheid I-CORE system. Two containers, e.g., cartridges, are used. An internal control is detected in both cartridges. The probe assignments for the agents are: Agent 1=Probes A, B; Agent 2=Probes C, D; Agent 3=Probes E, F; Control=Probe G.

Detectable label assignments and allocation of the probes between the two cartridges are shown in the following table.

| | Detectable Label Assignments and Cartridge Allocation for Probes | | | | | | | |
|---|---|---|---|---|---|---|---|---|
| | Cartridge A | | | | Cartridge B | | | |
| | Label 1 | Label 2 | Label 3 | Label 4 | Label 1 | Label 2 | Label 3 | Label 4 |
| Agent 1 | Probe A | | | | Probe B | | | |
| Agent 2 | | Probe C | | | | Probe D | | |
| Agent 3 | | | Probe E | | | | Probe F | |
| control | | | | Probe G | | | | Probe G |

The following call table next shows how the agent would be identified based on the results of the two cartridges.

| | Label Detected | |
|---|---|---|
| | Cartridge A | Cartridge B |
| Agent 1 | 1 | 1 |
| Agent 2 | 2 | 2 |
| Agent 3 | 3 | 3 |

Model for Identification of 4 Agents Using 4 Color Channels

In another embodiment, the method of the invention can detect 4 agents, using 2 markers per agent, and 1 control. In this embodiment, single probes for each of two agents are identically labeled and detected in one cartridge, and the second probes for each of the two agents are differentially labelled and detected in the second cartridge. In this embodiment, the method is used to identify four agents, e.g., organisms. Each organism can be identified by two markers, e.g., gene sequences. The markers are detected by fluorescently labeled probes. Detection of a gene sequence in a sample is performed using real time PCR and a four channel Cepheid I-CORE system. Two cartridges, e.g., containers are used. An internal control is detected in both cartridges. The probe assignments for the agents are: Agent 1=Probe A, B; Agent 2=Probe C, D; Agent 3=Probe E, F; Agent 4=Probes G and H, Control=Probe J.

Detectable label assignments and allocation of the probes between the two cartridges are shown in the following table.

| | Detectable Label Assignments and Cartridges Allocation for Probes | | | | | | | |
|---|---|---|---|---|---|---|---|---|
| | Cartridge A | | | | Cartridge B | | | |
| | Label 1 | Label 2 | Label 3 | Label 4 | Label 1 | Label 2 | Label 3 | Label 4 |
| Agent 1 | A | | | | B | | | |
| Agent 2 | C | | | | | D | | |
| Agent 3 | | E | | | | F | | |
| Agent 4 | | | G | | | | H | |
| control | | | | J | | | | J |

The following call table shows how the agent would be identified based on the results of the two cartridges.

|  | Label detected | |
|---|---|---|
|  | Cartridge A | Cartridge B |
| Agent 1 | 1 | 1 |
| Agent 2 | 1 | 2 |
| Agent 3 | 2 | 2 |
| Agent 4 | 3 | 3 |

Model for Identification of 5 Agents Using 4 Color Channels

In another embodiment, the method of the invention can detect 5 agents, using 2 markers per agent, and 1 control. In this embodiment, single probes for each of two agents are labelled identically and detected in one cartridge, and the second probe is labelled with a different label. In this case, the probe assignments for the agents are: Agent 1=Probes A, B; Agent 2=Probes C, D; Agent 3=Probes E, F; Agent 4=Probes G, H; Agent 5=Probes I, J; Control=Probe K.

Detectable label assignments and allocation of the probes between the two cartridges are shown in the following table.

| | Detectable Label Assignments and Cartridge Allocation for Probes | | | | | | |
|---|---|---|---|---|---|---|---|
| | Cartridge A | | | | Cartridge B | | |
| | Label 1 | Label 2 | Label 3 | Label 4 | Label 1 | Label 2 | Label 3 | Label 4 |
| Agent 1 | A | | | | B | | | |
| Agent 2 | C | | | | | D | | |
| Agent 3 | | E | | | | F | | |
| Agent 4 | | G | | | | | H | |
| Agent 5 | | | I | | J | | | |
| control | | | | K | | | | K |

The following call table shows the expected results.

|  | Label detected | |
|---|---|---|
|  | Cartridge A | Cartridge B |
| Agent 1 | 1 | 1 |
| Agent 2 | 1 | 2 |
| Agent 3 | 2 | 2 |
| Agent 4 | 2 | 3 |
| Agent 5 | 3 | 1 |

Model for Identification of 8 Agents Using 6 Color Channels

In another embodiment the invention is used for an assay utilizing a a system employing 6-color channels In this embodiment, 8 agents are identified using 2 sequences per agent, and employing 2 internal controls.

In this embodiment, single probes for each of two agents are identically labeled and detected in one cartridge. The second probes for each of the two agents are labelled differently. In this case, the probe assignments for the agents are: Agent 1=A, B, Agent 2=C, D, Agent 3=E, F, Agent 4=G, H, Agent 5=I, J, Agent 6=K, L, Agent 7=M, N, Agent 8=O, P, IC1=Q, IC2=R Detectable label assignments and allocation of the probes between the two cartridges are shown in the following 2 tables.

| | Detectable Label Assignments and Cartridge Allocation for Probes Cartridge A | | | | | |
|---|---|---|---|---|---|---|
| Label | 1 | 2 | 3 | 4 | 5 | 6 |
| Agent 1 | A | | | | | |
| Agent 2 | C | | | | | |
| Agent 3 | | E | | | | |
| Agent 4 | | G | | | | |
| Agent 5 | | | I | | | |
| Agent 6 | | | K | | | |
| Agent 7 | | | | M | | |
| Agent 8 | | | | O | | |
| IC1 | | | | | Q | |
| IC2 | | | | | | R |

| | Detectable Label Assignments and Cartridge Allocation for Probes Cartridge B | | | | | |
|---|---|---|---|---|---|---|
| Label | 1 | 2 | 3 | 4 | 5 | 6 |
| Agent 1 | B | | | | | |
| Agent 2 | | D | | | | |
| Agent 3 | | F | | | | |
| Agent 4 | | | H | | | |
| Agent 5 | | | J | | | |
| Agent 6 | | | | L | | |
| Agent 7 | | | | N | | |
| Agent 8 | P | | | | | |
| IC1 | | | | | Q | |
| IC2 | | | | | | R |

The following call table illustrates the expected results:

|  | Labels Detected | |
|---|---|---|
|  | Cartridge A | Cartridge B |
| Agent 1 | 1 | 1 |
| Agent 2 | 1 | 2 |
| Agent 3 | 2 | 2 |
| Agent 4 | 2 | 3 |
| Agent 5 | 3 | 3 |
| Agent 6 | 3 | 4 |
| Agent 7 | 4 | 4 |
| Agent 8 | 4 | 1 |
| IC1 | 5 | 5 |
| IC2 | 6 | 6 |

Model for Identification of 9 Agents Using 4 Color Channels

In another embodiment, more than 2 probes are labeled with the same detectable label. The number of probes that can be labeled with the same detectable label equals the number of detectable label that can be differentially detected, less those assigned to controls. By taking advantage of these additional combinations it is possible to determine many more agents than detectable labels available.

In one embodiment 9 agents are detected using 2 markers per agent, and 1 internal control. Three detectable labels are available for detection of agents, and 3 probes, each for a different agent, have the same detectable label. In this embodiment, the probe assignments for the agents are: Agent 1=probes A, B, Agent 2=probes C, D, Agent 3=probes E, F, Agent 4=probes G, H, Agent 5=probes I, J, Agent 6=probes K, L, Agent 7=probes M, N, Agent 8=probes O, P, Agent 9=probes U and V, and IC1=probe Q.

Detectable label assignments and allocation of the probes between the two cartridges are shown in the following table.

| | Detectable Label Assignments and Cartridge Allocation for Probes | | | | | | | |
|---|---|---|---|---|---|---|---|---|
| | Cartridge A | | | | Cartridge B | | | |
| | Label 1 | Label 2 | Label 3 | Label 4 | Label 1 | Label 2 | Label 3 | Label 4 |
| Agent 1 | A | | | | B | | | |
| Agent 2 | C | | | | | D | | |
| Agent 3 | E | | | | | | F | |
| Agent 4 | | G | | | H | | | |
| Agent 5 | | I | | | | J | | |
| Agent 6 | | K | | | | | L | |
| Agent 7 | | | M | | N | | | |
| Agent 8 | | | O | | | P | | |
| Agent 9 | | | U | | | | V | |
| IC | | | | Q | | | | Q |

The following call table illustrates the expected results.

| | Label Detected | |
|---|---|---|
| | Cartridge A | Cartridge B |
| Agent 1 | 1 | 1 |
| Agent 2 | 1 | 2 |
| Agent 3 | 1 | 3 |
| Agent 4 | 2 | 1 |
| Agent 5 | 2 | 2 |
| Agent 6 | 2 | 3 |
| Agent 7 | 3 | 1 |
| Agent 8 | 3 | 2 |
| Agent 9 | 3 | 3 |
| IC1 | 4 | 4 |

Detection Methods

The methods of the invention can use a number of different detection methods for detecting the presence or absence of a marker in a sample. A detection method typically employs at least one analytical reagent that binds to a specific marker, e.g., binds to a target macromolecular species and produces a detectable signal. These analytical reagents typically have two components: (1) a probe macromolecule, for example, an antibody or oligonucleotide, that can bind a target macromolecule (e.g., an antibody or a marker gene) with a high degree of specificity and affinity, and (2) a detectable label, such as a radioisotope or covalently-linked fluorescent dye molecule. In general, the binding properties of the probe macromolecule define the specificity of the detection method, and the detectability of the associated label determines the sensitivity of the detection method. The sensitivity of detection is in turn related to both the type of label employed and the quality and type of equipment available to detect it.

In one embodiment of the invention, real time PCR is used as the detection method. As described in more detail herein, a marker, e.g., a gene sequence, is amplified using real time PCR and the product is detected using a fluorescently labeled probe. In another embodiment, an immunoassay is used as the detection method. With this method of detection, the marker is, e.g., an antigen and the probe is a fluorescently labeled antibody. Various immunoassays are well known to one of skill in the art and include, e.g., ELISAs, RIAs, etc. One of skill in the art will readily appreciate that the methods of the invention can be used with any number of marker/probe/detection system combinations.

Detectable Labels

Detectable labels suitable for use in the present invention are compounds that are capable of producing, either directly or indirectly, a detectable signal. Examples of the types of detectable labels that can be used with the methods of the invention include, e.g., fluorescent or colored dyes, isotopic labels, enzymes, immune labels (e.g., antibodies or antigens) and the like. The labels may be incorporated into probes comprising for example, nucleic acids, proteins or antibodies. The label can directly or indirectly provide a detectable signal. Any method known in the art for conjugating the detectable label to a probe or other compound may be used.

In one embodiment, fluorescent labels are used in the methods of the invention. Useful labels in the present invention may include, but are not limited to, e.g., fluorescein, Texas red (commercially available from Molecular Probes), LIZ (commercially available from ABI), FAM, dROX (commercially available from ABI), Alexa647 (commercially available from Molecular Probes). Other fluorescent or chemiluminescent compounds that can be used are, e.g., fluorescein isothiocyanate, rhodamine, luciferin, and the like. In another embodiment, the detectable labels are radiolabels, e.g., $^3$H, $^{125}$I, $^{35}$S, $^{14}$C, or $^{32}$P. One of skill will appreciate that the detectable label can be an enzyme (e.g., horse radish peroxidase, alkaline phosphatase, beta-galactosidase and others commonly used in, e.g., an ELISA); biotin for staining with labeled streptavidin conjugate; magnetic beads, and calorimetric labels such as colloidal gold or colored glass or plastic (e.g., polystyrene, polypropylene, latex, etc.) beads. Patents teaching the use of such labels include U.S. Pat. Nos. 3,817,837; 3,850,752; 3,939,350; 3,996,345, 4,277,437; 4,275,149; and 4,366,241.

Detection Devices

Means of detecting labeled probes are well known to those of skill in the art. Thus, for example, fluorescent labels may be detected using a photodetector to detect emitted light, or radiolabels may be detected using photographic film or scintillation counters. Enzymatic labels are typically detected by providing the enzyme with a substrate and detecting the reaction product produced by the action of the enzyme on the substrate. Calorimetric labels are detected by visualizing the colored label.

In one embodiment, optical detection of real time PCR is used for detection of markers. PCR amplification of a marker nucleic acid is performed and real time detection of the amplified product is done using a fluorescently labeled probe. "Real-time PCR," or "TaqMan" assays are known in the art. As is known in the art, TaqMan probes contain two dyes, a reporter dye (e.g. 6-FAM) at the 5' end and a quencher dye (e.g. Black Hole Quencher or TAMRA) at the 3' end. During the reaction, the 5' to 3' nucleolytic activity of the Taq polymerase enzyme cleaves the probe between the reporter and the quencher thus resulting in increased fluorescence of the reporter. Accumulation of PCR products is detected directly by monitoring the increase in fluorescence of the reporter dye. Suitable PCR probes include, but are not limited to: TaqMan probes (Heid, C. A., et al., Genome Res. October 1996; 6(10):986-94 which is incorporated herein by reference), molecular beacons for example, fluorescent FAM, TAMRA, TET, or ROX in combination with a quenching dye such as DABCYL, (see, e.g., Marras SAE, et al., (1999) Genet Anal 14, 151-156 which is incorporated herein by reference) and more recently, Scorpions (DxS). Both TaqMan probes and molecular beacons allow detection of multiple DNA species (multiplexing) by use of different reporter dyes on different probes/beacons.

In another embodiment, the methods of the invention employ the Cepheid I-CORE system. The Cepheid I-CORE system utilizes 4 separate optical channels capable of detecting 4 fluorescent reporter dyes simultaneously. I-CORE technology is disclosed in U.S. Pat. No. 6,369,893, which is incorporated herein by reference.

Kits of the Invention

Another aspect of the invention includes kits for detecting at least two biological agents. Kits of the invention include at least two containers for analysis of the biological sample. Each container has a probe that can detect a marker for each biological agent that is to be detected; therefore, each container has at least two probes.

In one embodiment, the kit for detecting at least two biological agents includes two containers. Each container has two probes, one probe for detecting a first marker of the first biological agent and a second probe for detecting a first marker of the second biological agent.

In various embodiments, the kits of the invention can be used to detect the range of biological agents as described herein, e.g., bacteria cells, virus particles, biological toxins, and the like. Contemplated markers include those described herein, e.g., nucleic acids, proteins, and polysaccharides. In a preferred embodiment, the markers are nucleic acids, e.g., gene sequences. The probes that can be included in the kit include, e.g., nucleic acids and antibodies. The probes can be labeled using any number of detectable labels well-known to one of skill in the art and described in detail herein. In preferred embodiments, the detectable label is a fluorescent label.

Systems of the Invention

FIG. 1 shows a schematic block diagram of a system 10 for detecting at least first and second biological agents. The first agent comprises first and second markers, and the second agent comprises third and fourth markers. The system includes at least first and second containers 12A and 12B. The first container 12A houses reagents for detecting the first and third markers and the second container 12B houses reagents for detecting the second and fourth markers. Suitable containers include, but are not limited to, reaction vessels, tubes, cuvettes, or cartridges. In one particularly preferred embodiment, the first, second, third, and fourth markers comprise first, second, third, and fourth nucleic acid sequences, and the first and second containers are cartridges for extracting nucleic acid from a sample and for holding the nucleic acid for detection. Such cartridges are disclosed in U.S. Pat. Nos. 6,374,684 and 6,391,541 the disclosures of which are incorporated by reference herein.

The system 10 also includes at least one detector arranged to detect the presence or absence of the markers in the containers 12A and 12B. In a preferred embodiment, the system 20 includes at least first and second detectors 14A and 14B. The first detector 14A is arranged to detect the presence or absence of the markers in the first container 12A, and the second detector 14B is arranged to detect the presence or absence of the markers in the second container 12B. Although multiple detectors are preferred, it is well known that one could also use a single detector to detect markers in multiple containers by placing the single detector in optical communication with each container using optical devices such as optical fibers, wave guides, light pipes, etc. Detectors 14A and 14B are preferably fluorimeters for detecting and measuring fluorescent labels in the containers 12A and 12B. Such devices generally include at least one light source for exciting the fluorescent label and at least one photodetector for measuring the emitted fluorescence. These devices are well known in the art and widely commercially available, such as the I-CORE® modules from Cepheid cited above. Other suitable detectors include, but are not limited to, devices for detecting phosphorescent, chemiluminescent, or electrochemiluminescent labels The system 10 also includes at least one controller 16 (e.g., a computer or microprocessor) in communication with the at least one detector. The controller is programmed with computer-readable instructions to perform a series of operations, including the initiation of detection reactions in the containers 12A and 12B. In a preferred embodiment the markers identifying the agents are nucleic acids, the reagents housed in the first container 12A are nucleic acid probes specifically recognizing the first and the third markers, the reagents housed in the second container 12B are nucleic acid probes specifically recognizing the second and the fourth markers, and the detection reaction comprises nucleic acid amplification. Suitable nucleic acid amplification methods include polymerase chain reaction (PCR) and ligase chain reaction (LCR). Isothermic amplification reactions are suitable and can be used according to the methods of the invention. Examples of isothermic amplification reactions include strand displacement amplification (SDA) (Walker, et al. *Nucleic Acids Res.* 20(7):1691-6 (1992); Walker *PCR Methods Appl* 3(1):1-6 (1993)), transcription-mediated amplification (Phyffer, et al., *J. Clin. Microbiol.* 34:834-841 (1996); Vuorinen, et al. , *J. Clin. Microbiol.* 33:1856-1859 (1995)), nucleic acid sequence-based amplification (NASBA) (Compton, *Nature* 350(6313):91-2 (1991), rolling circle amplification (RCA) (Lisby, *Mol. Biotechnol.* 12(1): 75-99 (1999)); Hatch et al., Genet. Anal. 15(2):35-40 (1999)) and branched DNA signal amplification (bDNA) (see, e.g., Iqbal et al., *Mol. Cell Probes* 13(4):315-320 (1999)). Other amplification methods known to those of skill in the art include CPR (Cycling Probe Reaction), SSR (Self-Sustained Sequence Replication), SDA (Strand Displacement Amplification), QBR (Q-Beta Replicase), Re-AMP (formerly RAMP), RCR (Repair Chain Reaction), TAS (Transcription Based Amplification System), and HCS.

The system 10 optionally includes at least one temperature controller. The temperature controller is optional because not all detection reactions require control of the temperature of the reaction mixture. However, in preferred embodiments where the detection reaction is nucleic acid amplification, the system 10 includes at least one temperature controller, such as temperature controllers 18A and 18B for subjecting reaction mixtures in containers 12A and 12B to nucleic acid amplification conditions. Although multiple temperature controllers are preferred, it is well known that one could also use a single temperature controller (e.g., a metal block for holding multiple sample containers or a forced air system for heating/cooling multiple containers) to control the temperature of reaction mixtures in multiple containers. In particularly preferred embodiments where the detection reaction is PCR, the at least one temperature controller is a thermal cycler for heating and cooling the reaction mixtures in the containers 12A and 12B according to programmed time/temperature profiles. Thermal cyclers with built-in detector(s) operating under computer control are well known in the art and include, e.g., Cepheid's Smart Cycler® system (e.g., U.S. Pat. Nos. 6,369,893 and 6,565, 815); ABI thermocyclers (e.g., U.S. Pat. Nos. 5,656,493 and 5,038,852); and Roche's Lightcycler (e.g., U.S. Pat. Nos. 5,455,175 and 5,935,522).

Figure 2:
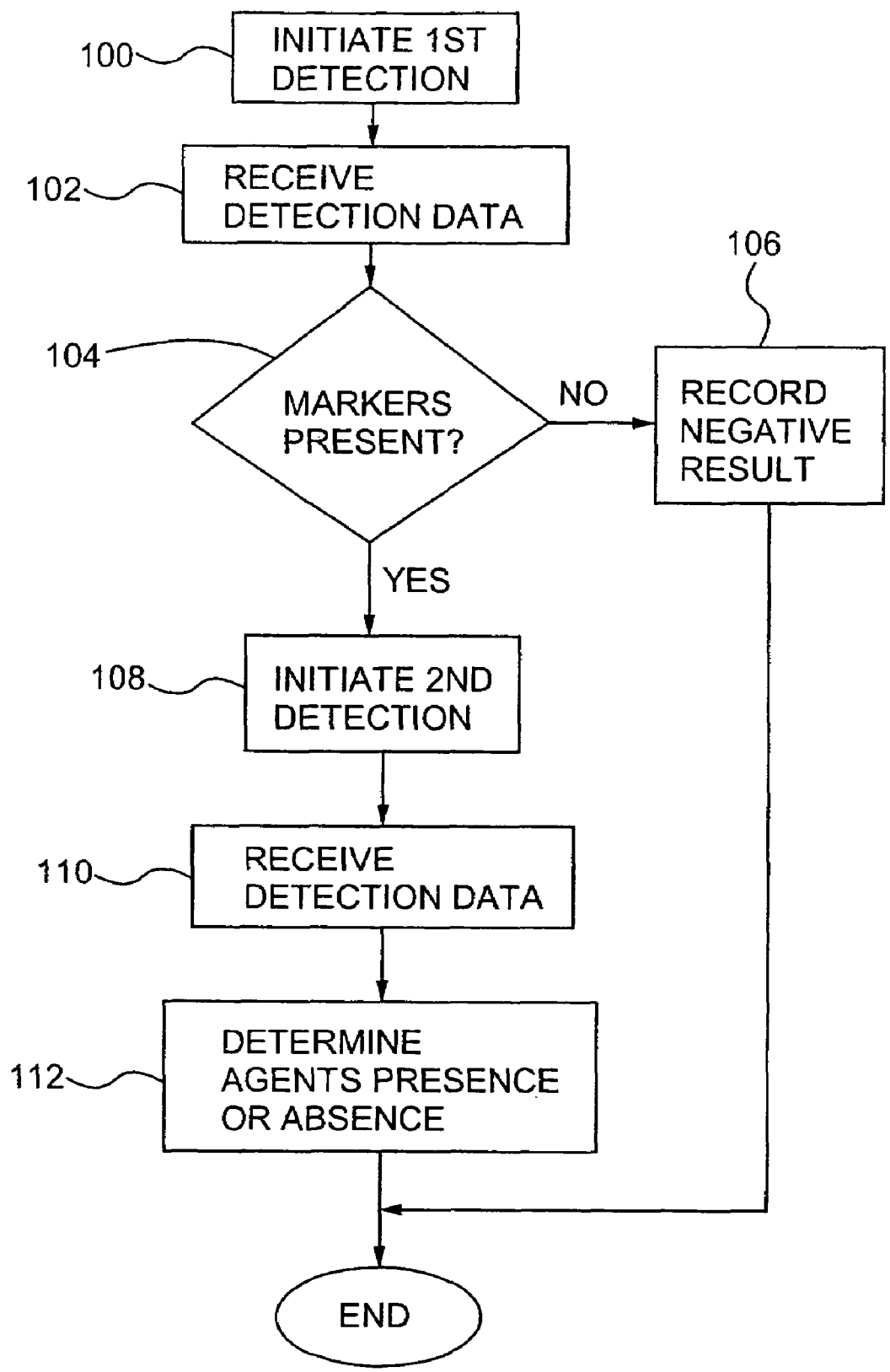
FIG. 2 is a flow chart showing program steps executed by the controller of the system of FIG. 1.

FIG. 2 is a flow diagram showing the steps that the controller 16 is programmed to execute to detect the presence or absence of multiple biological agents. In step 100, the controller 16 initiates a detection reaction in the first container 12A. In step 102, the controller 16 receives data from the detector 14A. In decision step 104, the controller 16 determines from the data the presence or absence of the first and third markers in the first container 12A. This is preferably accomplished by comparing the detection signal for each marker to a minimum threshold value. If neither of the first or third markers is present in the first container, then the controller records a negative result in step 106 and the detection reaction in the second container 12B need not be run. If, however, either of the first or third markers is detected in the first container 12A, then the controller 16 initiates a second detection reaction in the second container, step 108. In step 110, the controller 16 receives detection data from the detector 14B. In step 112, the controller determines from the detection data the presence or absence of the second or fourth markers in the second container, and thus the presence or absence of the first and second agents. The presence of the first and second markers in the first and second containers, respectively, indicates the presence of the first biological agent in a sample, and the presence of the third and fourth markers in the first and second containers, respectively, indicates the presence of the second biological agent in the sample.

Figure 3:
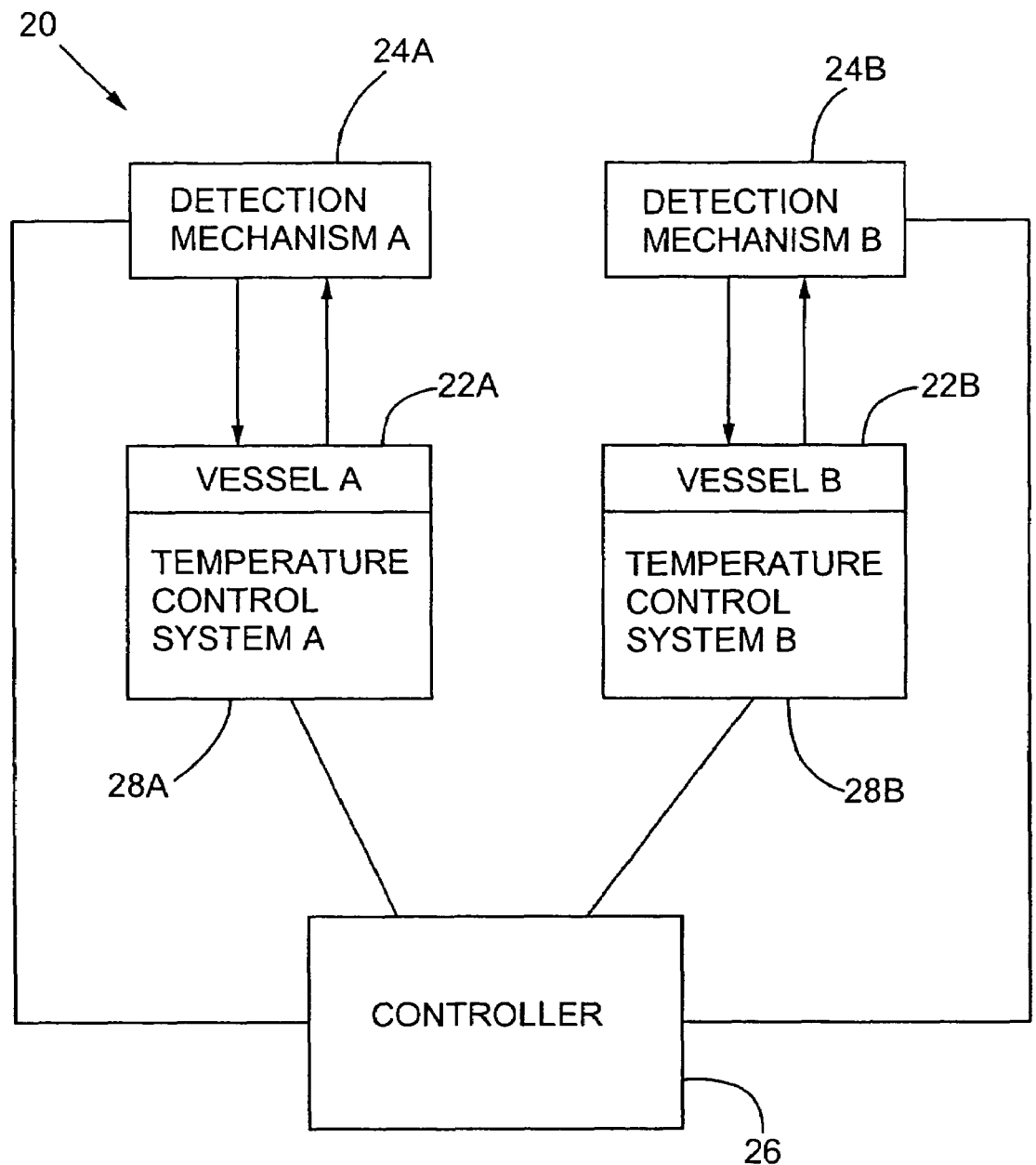
FIG. 3 shows a schematic block diagram of a system for detecting at least first and second biological agents according to another embodiment of the invention.

FIG. 3 shows an automated system 20 for determining the presence or absence of a plurality of biological agents according to another embodiment of the invention. Each of the agents comprises respective first and second nucleic acid sequences that differentiate the agent from the other agents. The system 20 includes at least one temperature control system, such as temperature control systems 28A and 28B, for subjecting first and second reaction mixtures suspected of containing the agents to nucleic acid amplification conditions in reaction vessels 22A and 22B, respectively. The first reaction mixture in reaction vessel 22A contains reagents and probes for amplifying and detecting the first nucleic acid sequence of each of the agents. The second reaction mixture in reaction vessel 22B contains reagents and probes for amplifying and detecting the second nucleic acid sequence of each of the agents. Although multiple temperature control systems are preferred, it is well known that one could also use a single temperature control system (e.g., a metal block for holding multiple sample containers or a forced air system for heating/cooling multiple containers) to control the temperature of reaction mixtures in multiple vessels. In particularly preferred embodiments where the detection reaction is PCR, the at least one temperature control system is a thermal cycler for heating and cooling the reaction mixtures in the vessels 22A and 22B according to programmed time/temperature profiles. Thermal cyclers with built-in detector(s) operating under computer control are well known in the art and include, e.g., Cepheid's Smart Cycler® system (e.g., U.S. Pat. Nos. 6,369,893 and 6,565,815); ABI thermocyclers (e.g., U.S. Pat. Nos. 5,656,493 and 5,038,852); and Roche's Lightcycler (e.g., U.S. Pat. Nos. 5,455,175 and 5,935,522).

Suitable nucleic acid amplification reactions include polymerase chain reaction (PCR) and ligase chain reaction (LCR). Isothermic amplification reactions are suitable and can be used according to the methods of the invention. Examples of isothermic amplification reactions include strand displacement amplification (SDA) (Walker, et al. *Nucleic Acids Res.* 20(7):1691-6 (1992); Walker *PCR Methods Appl* 3(1):1-6 (1993)), transcription-mediated amplification (Phyffer, et al., *J. Clin. Microbiol.* 34:834-841 (1996); Vuorinen, et al. , *J. Clin. Microbiol.* 33:1856-1859 (1995)), nucleic acid sequence-based amplification (NASBA) (Compton, *Nature* 350(6313):91-2 (1991), rolling circle amplification (RCA) (Lisby, *Mol. Biotechnol.* 12(1):75-99 (1999)); Hatch et al., *Genet. Anal.* 15(2):35-40 (1999)) and branched DNA signal amplification (bDNA) (see, e.g., Iqbal et al., *Mol. Cell Probes* 13(4):315-320 (1999)). Other amplification methods known to those of skill in the art include CPR (Cycling Probe Reaction), SSR (Self-Sustained Sequence Replication), SDA (Strand Displacement Amplification), QBR (Q-Beta Replicase), Re-AMP (formerly RAMP), RCR (Repair Chain Reaction), TAS (Transcription Based Amplification System), and HCS.

The system 20 also includes at least one detection mechanism arranged to detect probe signals from the reaction mixtures in the vessels 22A and 22B. In a preferred embodiment, the system 20 includes at least first and second detection mechanisms 24A and 24B. The first detection mechanism 24A is arranged to detect the presence or absence of the target nucleic acid sequences in the first vessel 22A, and the second detection mechanism 24B is arranged to detect the presence or absence of the target nucleic acid sequences in the second vessel 22B. Although multiple detection mechanisms are preferred, it is well known that one could also use a single detector to detect markers in multiple containers by placing the single detector in optical communication with each container using optical devices such as optical fibers, wave guides, light pipes, etc. Detection mechanisms 24A and 24B are preferably fluorimeters for detecting and measuring fluorescent labels in the reaction mixtures. Such devices generally include at least one light source for exciting the fluorescent label and at least one photodetector for measuring the emitted fluorescence. These devices are well known in the art and widely commercially available, such as the I-CORE® modules from Cepheid cited above. Other suitable detection mechanisms include, but are not limited to, devices for detecting phosphorescent, chemiluminescent, or electrochemiluminescent labels.

The system 20 also includes at least one controller 26 (e.g., a computer or microprocessor) in communication with the temperature control systems 28A and 28B and with the detection mechanisms 24A and 24B. The controller is programmed to perform steps to determine the presence or absence of a plurality of biological agents.

Figure 4:
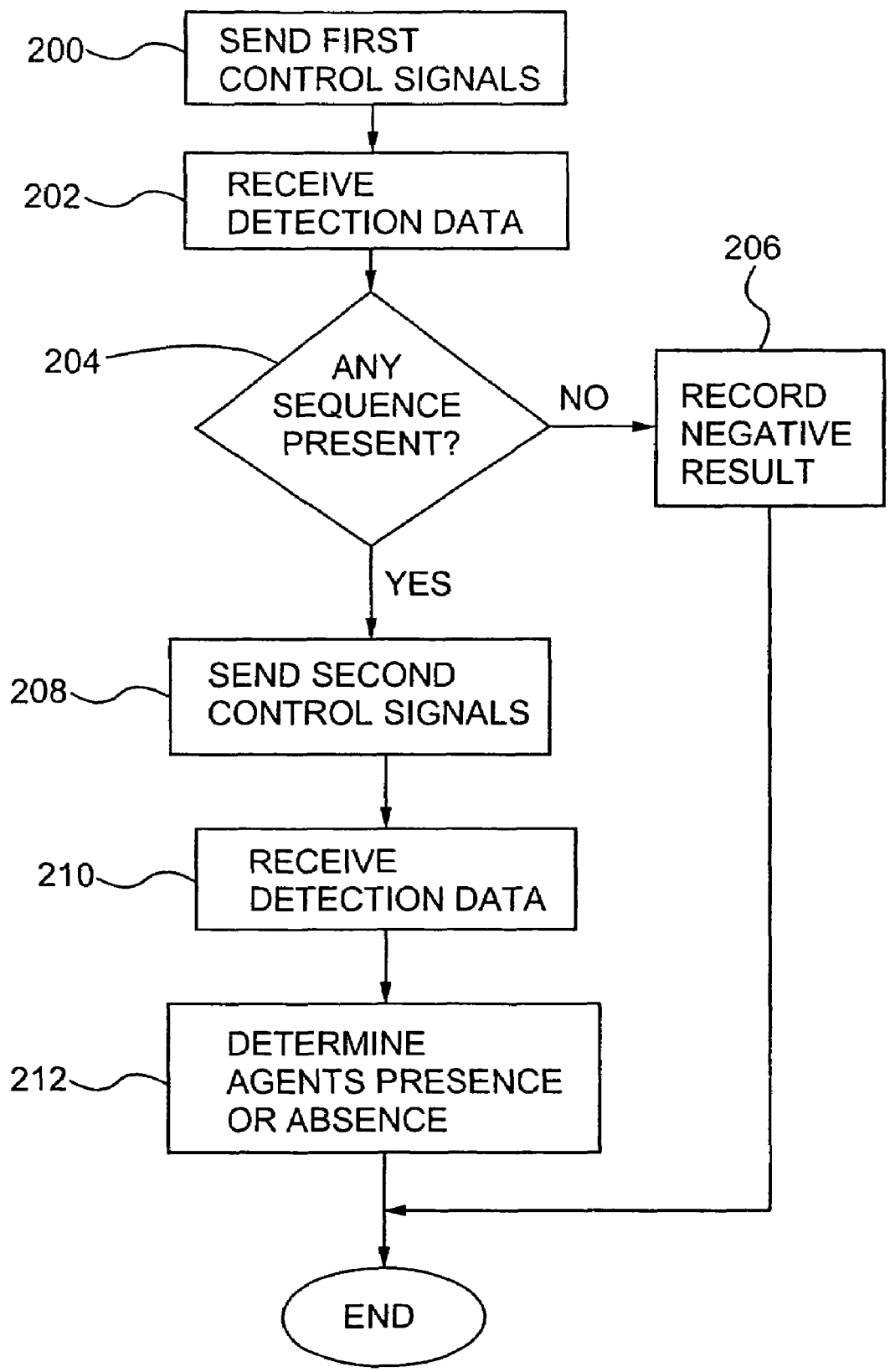
FIG. 4 is a flow chart showing program steps executed by the controller of the system of FIG. 3.

FIG. 4 is a flow diagram showing the steps that the controller 26 is programmed to perform to detect the presence or absence of multiple biological agents. In step 200, the controller 26 sends control signals to the first temperature control system 28A to subject the first reaction mixture in the vessel 22A to nucleic acid amplification conditions. In step 202, the controller 26 receives probe signal data from the detector 24A. In decision step 204; the controller 26 determines from the probe signals received from the first reaction mixture in vessel 22A if the first nucleic acid sequence of any of the agents is present in the first reaction mixture. This is preferably accomplished by comparing the probe signal for each target nucleic acid sequence to a minimum threshold value. If none of the target nucleic acid sequences is detected in the first reaction mixture, then the controller records a negative result in step 206 and the amplification reaction in the second vessel 22B does not need to be run. If, however, the first target nucleic acid sequence of any of the agents is detected in the first reaction mixture in vessel 22A, then the controller 26 sends control signals to the second temperature control system 28B to subject the second reaction mixture in the vessel 22B to nucleic acid amplification conditions, step 208. In step 210, the controller 26 receives detection data from the detector 24B. In step 212, the controller determines from probe signals received from the second reaction mixture if the second nucleic acid sequence of any of the agents is present in the second reaction mixture, and thus the presence or absence of the multiple agents. The presence of the first and second nucleic acid sequences of any of the agents (detected in separate reactions) is indicative of the presence of that agent.

Biological Agents

The methods of the invention are used to analyze samples for the presence or absence of any number of different biological agents. Exemplary biological agents identified using the methods of the invention include, but are not limited to, nucleic acids, proteins including protein complexes, cells, e.g., bacteria cells, virus particles, and complex carbohydrates.

Sample Collection and Processing

Samples that possibly contain biological agents detectable with the present invention can be found in both biological and environmental sources. Exemplary biological cultures include cell cultures, e.g., bacterial cultures, cellular extracts, blood, tissue samples, bodily and cellular secretions and excretions and the like. Environmental sources include the air, aquifers, soil, rocks, ice, sea water, refuse and the like.

Biological samples for analysis using the present invention can be collected using any suitable technique known in the art. By way of example, blood can be drawn with a hypodermic needle; tissue samples collected by scraping or surgically removing a portion of the tissue; cell cultures may be pelleted by, for example, centrifugation of a cell suspension. Cellular extracts can be fractionated using any of a variety of techniques including, but not limited to, centrifugation, chromatography, differential salt and/or organic solvent precipitation, electrophoresis and the like.

Environmental samples can be collected using any known technique. For example, airborne biological agents can be partitioned into a solution by bubbling or percolating air through a liquid solvent, thereby allowing the airborne biological agents to partition into the liquid phase, preferably undergoing concomitant concentration. Biological agents in liquid environmental sources can be concentrated and/or purified through distillation or filtration, chromatographic separation and the like. Biological agents on solid surfaces in the environment can be collected by wiping or swabbing the solid surface, with the biological agent then being rescued from the wipe or swab. Solids that are in the form of powders or can be reduced to powders also can be extracted using aqueous or organic solvents known to those of ordinary skill in the art.

Once collected, samples can be in a purified/partially purified form or in a complex mixture that is in a liquid, semi-liquid, or suspension, preferably in an aqueous state.

Extracting Nucleic Acids and Proteins From Biological Samples

In some embodiments of the invention, it is desirable to treat the sample that is suspected to include a biological agent, e.g., a cell or virus, before analysis of the sample. For example, cell lysis accompanied by extraction of nucleic acids can be performed for ease of detection by methods including, e.g., real time PCR. The extraction of nucleic acids from cells or viruses can be performed by physical, chemical, or other means, or by a combination of such means.

In one embodiment, the methods of the invention utilize the Cepheid fluidic cartridges. These cartridges are fully disclosed in U.S Pat. Nos. 6,374,684; 6,391,541; and 6,440,725, all of which are incorporated by reference in their entirety. These fluidic cartridges (e.g., containers) automatically carry out the nucleic acid extraction from a variety of sample types. The cartridges perform some or all of the following functions: reagent containment and delivery; sample and reagent aliquoting and mixing; cell separation and concentration; rapid cell lysis using ultrasonic techniques; DNA or RNA capture, enrichment, and purification; and preparation of reaction mixture and filling of integrated reaction tube (e.g., container).

Other methods of sample preparation for extraction of nucleic acid and/or protein markers in order to use the methods of the invention are known to one of skill in the art. Physical means include the mechanical disruption of the cells, such as by the vibration of glass or plastic beads or other particles, by impacting the target cells or viruses onto sharp microstructures, or by a pressure instrument that passes a solution of microorganisms through a very small diameter hole under high pressure thereby breaking open the cells. Thermal energy transfer, such as by heating a virus suspension to 95 C or by repeated freeze-thawing of activated bacterial spores to disrupt cell walls, may also be used.

The mechanical disruption of target cells or viruses can be accomplished with interactive regions designed to tear the surface membrane or cell wall of the target organism via shearing or vibration. Vibration can be accomplished by containing glass or other beads in a chamber, and by coupling to the chamber a piezomembrane also incorporated into the cartridge. Alternatively, an ultrasonic transducer, such as an ultrasonic horn, may be coupled to a wall of the chamber to transfer ultrasonic energy to the cells. The frequency and amplitude of the ultrasound is tuned to correspond with the resonant frequency of the target cells and optimized to effect lysis with minimal heating or cavitation, though the latter may be required for efficient lysis. Some ultrasonic methods are disclosed by Murphy et al. in U.S. Pat. No. 5,374,522, and by Li in U.S. Pat. No. 4,983,523.

Chemical lysing can be employed alone or in combination with physical or ultrasonic lysing. Typical chemical lysing agents fall into several categories, such as enzymes, detergents, and chaotropes. Lysosyme is an enzyme that hydrolytically attacks the cell walls of many bacteria; trypsin is a protease enzyme that breaks the cell membrane of most eukaryotic cells. Other proteases with specificity for certain peptide sequences can be employed and are preferred if the target moiety is liable to certain proteases. Proteinase K is often used because it also digests nuclear proteins and host cell enzymes that may interfere with polymerase chain reaction (PCR). For eucaryotic cells, detergents such as Triton X-100 or sodium dodecyl sulfate solubilize the cell membrane and release intracellular contents. Chaotropes such as guanidine isothiocyanate or urea can be used to lyse cells and have the additional benefit of inhibiting RNAses that can destroy target RNA. Examples of chemical methods are described in U.S. Pat. No. 5,652,141 to Henco et al. and U.S. Pat. No. 5,856,174 to Lipshutz et al.

Other methods of cell extraction may also be used, e.g., employing a channel with restricted cross-sectional dimensions so that shear stress causes cell lysis when the sample is passed through the channel at sufficiently high pressure. Alternatively, cell extraction and denaturing of contaminating proteins may be carried out by applying an alternating electrical current to the sample.

Markers and Probes

The methods of the invention include detecting markers from each biological agent that is to be identified. Detecting a marker includes distinctly identifying macromolecular, microscopic or molecular characteristics of the biological agent under analysis. Distinctly identifying characteristics serving as markers of the present invention do not have to uniquely identify the biological agent, but markers preferably indicate with at least 80%, more preferably 85%, 90%, 91%, 92%, 93%, 94%, 95%, 98%, 99% or greater certainty that the biological agent is present when the marker is detected. Therefore, identification of more than one marker, e.g., at least 2 markers, for a biological agent in a sample indicates with near certainty that the biological agent is present in the sample. Thus, in most situations two markers per agent are preferable to differentiate two agents.

Preferred markers suitable for use in the present invention include any molecular or macromolecular characteristic that can be recognized with a probe of the present invention. Suitable marker-probe combinations include receptor-ligand, enzyme-substrate, antigen (or epitope)-antibody, and complementary nucleic acid sequences.

Various embodiments of the invention use probes that are nucleic acids (e.g., complementary oligonucleotides), proteins, (e.g., ligands, substrates, antigens, antibodies,) and the like. It is contemplated that any probe used in the present invention will be labeled with a detectable label so that the probe is detectable in an appropriate detection system.

Markers and/or probes can be nucleic acids. In one embodiment, at least one marker is a nucleic acid sequence of the biological agent, e.g., bacterial cell or virus. Accordingly, in this example, the probe is a complementary oligonucleotide that hybridizes to the nucleic acid sequence. As a general rule, the number of sequences needed to support a highly specific confirmation result range from two to six sequences. In most cases, two sequences are preferable to differentiate an agent, e.g., an organism, from potentially rare nearest neighbor organisms, plasmid-cured strains, or uncharacterized or unexpected background.

A protein probe is preferably an affinity binding partner, preferably an immunoaffinity binding partner, of the marker of interest. For example, where the marker is an enzyme, the probe may be a naturally occurring substrate of the enzyme, or a synthetically-derived analog substrate. If the marker is a receptor, the probe may be a natural or a synthetic ligand of the receptor. Preferably protein probes are antibodies, or antibody fragments, that specifically recognize epitope marker(s). Accordingly, in an alternate embodiment, at least one marker is an antigen of the biological agent and the probe is an antibody.

Nucleic Acid Probes

Many different nucleic acid hybridization probes are suitable for the practice of the invention. Numerous types of probes are capable of hybridizing to and detecting particular polynucleotide sequences. In some cases, the probe comprises a fluorophore or enzyme, which allows for the detection of the binding of the probe to its complement.

A nucleic acid probe may be single-stranded or double-stranded. A nucleic acid of the present invention will generally contain phosphodiester bonds, although in some cases, as outlined below, nucleic acid analogs are included that may have alternate backbones. The nucleic acid may be DNA, both genomic and cDNA, RNA or a hybrid, where the nucleic acid contains any combination of deoxyribo- and ribo-nucleotides, and any combination of bases, including uracil, adenine, thymine, cytosine, guanine, inosine, xanthine hypoxanthine, isocytosine, isoguanine, etc., including nucleotide analogs, and modified nucleosides such as amino modified nucleosides.

Probe concentration should be sufficient to bind to the amount of target or control sequences that are amplified so as to provide an accurate assessment of the quantity of amplified sequence. Those of skill in the art will recognize that the amount of concentration of probe will vary according to the binding affinity of the probe as well as the quantity of sequence to be bound Typically, for signal generation, the probes utilize a change in the fluorescence of a fluorophore due to a change in its interaction with another molecule or moiety brought about by changing the distance between the fluorophore and the interacting molecule or moiety. Alternatively, other methods of detecting a polynucleotide in a sample, including the use of radioactively-labeled probes, are provided.

Fluorescence-based assays may rely for signal generation on fluorescence resonance energy transfer, or "FRET". FRET is known in the art. Briefly, the method measures a change in fluorescence caused by a change in the distance separating a first fluorophore from an interacting resonance energy acceptor, either another fluorophore or a quencher. Combinations of a fluorophore and an interacting molecule or moiety, including quenching molecules or moieties, are known as "FRET pairs." The mechanism of FRET-pair interaction requires that the absorption spectrum of one member of the pair overlaps the emission spectrum of the other member, the first fluorophore. If the interacting molecule or moiety is a quencher, its absorption spectrum must overlap the emission spectrum of the fluorophore (Stryer, L., Ann. Rev. Biochem. 47: 819-846 (1978); Biophysical Chemistry part II, Techniques for the Study of Biological Structure and Function, C. R. Cantor and P. R. Schimmel, pages 448-455 (W. H. Freeman and Co., San Francisco, U.S.A., 1980); and Selvin, P. R., Methods in Enzymology 246: 300-335 (1995)). Non-FRET fluorescent probes, such as those described in, e.g., Tyagi et al., U.S. Pat. No. 6,150,097, can also be used.

Protein Probes

Methods for assaying using peptide sequences or peptide analogs are provided by the invention. Protein probes may comprise a fluorescent label, a radioactive label, or any acceptable label known in the art. In some embodiments the target protein may be labeled instead of the probe.

In one aspect of the invention, the target to be detected preferably comprises a peptide sequence or a peptide-like analog sequence, such as, e.g., a dipeptide, tripeptide, polypeptide, protein or a multi-protein complex. In one aspect, the target to be detected is a protein having at least one receptor site for the probe.

Detectable proteins of the invention may be detected by a probe comprising an amino acid or amino acid analog. For example, suitable probes can comprise a single amino acid, single amino acid analog, a peptide-like analog, peptidoid, peptidomimetic, peptide, dipeptide, tripeptide, polypeptide, protein or a multi-protein complex.

A variety of binding complexes can be assayed with the method of the invention. In some embodiments, the invention is used to analyze binding characteristics (including the presence or absence of binding, and the binding affinity)

between proteins and other amino acid based or amino acid analog based compounds. Suitable proteins for analysis include, e.g., wild-type, mutant, isolated, in vitro translated, and/or synthesized. The invention is may also be used for analyzing binding of ligands to protein receptors.

For example, one binding complex that can be useful for practicing the methods of the invention include specific binding of a fluorescently-labeled peptide to a single protein or multi-protein complex. In this case the specific protein is either directly bound to the labeled protein probe, or is present in a multi-protein complex and is thus interacting with one or more other proteins in the complex, but not necessarily directly interacting with the labeled probe.

Similarly, the invention also enables detecting the binding of an unlabeled compound to at least one member of a complex of complexed compounds, wherein at least one of the complexed compounds is labeled for, e.g., fluorescent intensity measurements. The labeled compound and the unlabeled compound need not even directly interact for detection to occur. Thus, the invention enables detecting a protein through indirect or direct influence on the binding characteristics of a labeled probe to a target.

Antibodies

In one embodiment, markers are detected using antibodies. Antibody probes can be both polyclonal and monoclonal antibodies. Antibody probes can also be genetically engineered forms such as chimeric antibodies (e.g., humanized murine antibodies) and heteroconjugate antibodies (e.g., bispecific antibodies), as well as antigen binding forms of antibodies, including fragments with antigen-binding capability (e.g., Fab', F(ab')$_2$, Fab, Fv and rIgG). See also, Pierce Catalog and Handbook, 1994-1995 (Pierce Chemical Co., Rockford, Ill.). See also, e.g., Kuby, J., *Immunology*, $3^{rd}$ Ed., W.H. Freeman & Co., New York (1998). The term also refers to recombinant single chain Fv fragments (scFv). The term antibody may also include bivalent or bispecific molecules, diabodies, triabodies, and tetrabodies. Bivalent and bispecific molecules are described in, e.g., Kostelny et al. (1992) *J Immunol* 148:1547, Pack and Pluckthun (1992) *Biochemistry* 31:1579, Hollinger et al., 1993, supra, Gruber et al. (1994) *J Immunol*:5368, Zhu et al. (1997) *Protein Sci* 6:781, Hu et al. (1996) *Cancer Res.* 56:3055, Adams et al. (1993) *Cancer Res.* 53:4026, and McCartney, et al. (1995) *Protein Eng.* 8:301.

Polysaccharide Probes

Another embodiment utilizes polysaccharide markers and probes that recognize these markers, e.g., lectins and carbohydrate binding proteins. Polysaccharide residues can be located in biological agents, e.g., in glycoproteins and glycolipids. These markers can be detected with labeled probes, e.g., fluorescently labeled glycoproteins. Suitable polysaccharide based marker/probe systems are well-known to one of skill in the art and are commercially available, e.g., from Molecular Probes.

EXAMPLES

Below are examples of specific embodiments for carrying out the present invention. The examples are offered for illustrative purposes only, and are not intended to limit the scope of the present invention in any way. Efforts have been made to ensure accuracy with respect to numbers used (e.g., amounts, temperatures, etc.), but some experimental error and deviation should, of course, be allowed for.

The practice of the present invention can employ conventional methods of protein chemistry, biochemistry, recombinant DNA techniques and nucleic acid amplification, within the skill of the art. Such techniques are explained fully in the literature. See, e.g., T. E. Creighton, *Proteins: Structures and Molecular Properties* (W.H. Freeman and Company, 1993); A. L. Lehninger, *Biochemistry* (Worth Publishers, Inc., current addition); Sambrook, et al., *Molecular Cloning: A Laboratory Manual* (2nd Edition, 1989); *Methods In Enzymology* (S. Colowick and N. Kaplan eds., Academic Press, Inc.); *Remington's Pharmaceutical Sciences*, 18th Edition (Easton, Pa.: Mack Publishing Company, 1990); Carey and Sundberg *Advanced Organic Chemistry* $3^{rd}$ *Ed*. (Plenum Press) Vols A and B (1992).

Briefly, as described in more detail below, multiplexed 4 channel real time PCR was used to detect two nucleic acid markers for each of 3 biological agents in a sample. Nucleic acid probes were labeled with one of four different fluorescent dyes. The method was used to identify the biological agents in the sample. Those of skill in the art will recognize that the methods set forth herein are broadly applicable to a number of assay systems, using any label, e.g., fluorophore, detectable at the single molecule level, and in the detection of a wide range of target moieties.

Two markers per agent were detected and are described as follows: *Bacillus anthracis* Ames strain gene A (GenBank accession number NC003980 ; *Bacillus anthracis* Ames strain gene B (GenBank accession number NC003981); Group B *streptococcus* (GBS) genes A and B (GenBank accession number X72754); and *Bacillus globigii* (Bg) genes A and B (GeneBank accession number Z28592.1). Each reaction mixture also contained reagents to enable the detection of an internal control plasmid (IC1) (US patent application US 20030211527, incorporated herein in its entirely for all purposes).

PCR primers and probes for amplification and detection of the marker genes were designed using the sequences disclosed above and principles well-known to one of skill in the art and described in more detail herein. Probes were labeled using either LIZ (detectable using color channel 1), Alexa 647 (detectable using color channel 1), FAM (detectable using color channel 2), dROX (detectable using color channel 3), or VIC (detectable using color channel 4).

Primer and probes were designed using the marker gene sequence and primer design software that is commonly available, e.g., Oligo 6 (Molecular Biology Insights, Inc); Primer3 (Whitehead Institute for Biomedical Research); and Primer Express (Applied Biosystems, Inc.). One skilled in the art will recognize that design of the primers generally followed a set of rules: primers were 17-28 bases in length; base composition was 50-60% (G+C); primers ended (3') in a G or C, or CG or GC; Tms were preferably between 55-80° C.; runs of three or more Cs or Gs at the 3'-ends of primers (that can promote mispriming at G or C-rich sequences) were preferably avoided; 3'-ends of primers were preferably not complementary; primer self-complementarity (ability to form secondary structures such as hairpins) was preferably avoided; for multiplex assays, the Tms of each primer were preferably similar; the amplicons that were generated were preferably of similar sizes and between 100 to 250 bp.

For TaqMan probes, similar rules are followed that are well known to one of skill in the art, including: melting temperature (Tm) of the probe is preferably 68-70° C.; G–C contents is preferably in the 30-80% range; runs of an identical nucleotide are avoided, especially for G; Gs on the 5' end are preferably avoided; the strand that gives the probe more Cs than Gs is preferably selected. In addition, if the TaqMan probe is designed for allelic discrimination, the position of the polymorphic site (mismatch) should be approximately in the middle third of the sequence.

Example 1

Identification of Three (3) Different Biological Agents in a Sample

Preparation of Reaction Mixtures

Two reaction mixtures were prepared to enable the real time detection of three different organisms: *Bacillus anthracis* Ames strain (Ames); Group B *streptococcus* (GBS); and *Bacillus globigii* (Bg). Each reaction mixture also contained reagents to enable the detection of an internal control plasmid (IC1). Three color channels were used for detection.

Reaction Mixture 1 (master mix volume of 81 µL) contained 600 nM upper primer, 600 nM lower primer and 100 nM FAM labeled probe for the detection of *B. anthracis* gene A; 500 nM upper primer, 500 nM lower primer and 300 nM FAM labeled probe for the detection of GBS gene A; 500 nM upper primer, 500 nM lower primer and 500 nM Alexa 647 labeled probe for the detection of Bg gene A; 200 nM upper primer, 200 nM lower primer and 75 nM dROX labeled probe for the detection of the IC plasmid; 4 fg IC plasmid DNA; and 9.0 µL 4× Cepheid lyophilization buffer. The master mix was used to resuspend a lyophilized enzyme reagent bead containing 10 units AmpliTaq polymerase/Taq polymerase antibody complex. The final $MgCl_2$ concentration was approximately 6 mM.

Reaction Mixture 2 (master mix volume of 81 µL) contained 400 nM upper primer, 400 nM lower primer and 75 nM LIZ labeled probe for the detection of *B. anthracis* gene B; 500 nM upper primer, 500 nM lower primer and 200 nM FAM labeled probe for the detection of GBS gene B; 500 nM upper primer, 500 nM lower primer and 300 nM Alexa 647 labeled probe for the detection of Bg gene B; 200 nM upper primer, 200 nM lower primer and 75 nM dROX labeled probe for the detection of the IC plasmid; 4fg IC plasmid DNA and 9.0 µL 4× Cepheid lyophilization buffer. The master mix was used to resuspend a lyophilized enzyme reagent bead containing 10 units AmpliTaq polymerase/Taq polymerase antibody complex. The final $MgCl_2$ concentration was approximately 6 mM.

The following is a tabular representation of the probe labels and cartridge assignments for this experiment, and the expected results (call table):

|  | Cartridge 1 | | | Cartridge 2 | | |
| --- | --- | --- | --- | --- | --- | --- |
| Agent | Channel 1 | Channel 2 | Channel 3 | Channel 1 | Channel 2 | Channel 3 |
| Ames |  | Ames gene A |  |  | Ames gene B |  |
| GBS |  | GBS gene A |  |  | GBS gene B |  |
| Bg | Bg gene A |  |  | Bg gene B |  |  |
| IC1 |  |  | IC1 |  |  | IC1 |

| Agent | Cartridge 1 | Cartridge 2 |
| --- | --- | --- |
| Ames strain | 2 | 1 |
| GBS | 2 | 2 |
| Bg | 1 | 1 |
| IC1 | 3 | 3 |

Detection of *B. anthracis* Ames Strain

*B. anthracis* Ames strain spores were sonicated to release DNA and 4.0 µL of 63 cfu/µL was added to Reaction Mixture 1 and to Reaction Mixture 2. Each reaction was performed in triplicate; identical results were obtained for all three reactions in a set. Three 25 μL aliquots of each mixture were divided into three 25 μL I-CORE tubes. Thermocycling was carried out on Smart Cycler® instruments using the following protocol: hold at 95° C. for 3 minutes; then 45 cycles of 95° C., 5 seconds; 60° C. 14 seconds; 72° C. 5 seconds. Real time fluorescence data was collected during the 60° C. annealing step.

The results are presented in the following table. A positive signal was detected in channel 2 of Reaction Mixture 1 and channel 1 of in Reaction Mixture 2. This result confirmed the presence of the biological agent *B. anthracis* Ames strain in the sample. The lack of channel 2 signal in Reaction Mixture 2 confirmed the absence of GBS in the sample. The lack of channel 1 signal in Reaction Mixture 1 confirmed the absence of Bg in the sample. A positive signal for channel 3 in both reactions confirmed the presence of IC1 in both reactions and no inhibition of the assay.

| | Cartridge 1 | Cartridge 2 |
|---|---|---|
| Channel 1 | --- | +++ |
| Channel 2 | +++ | --- |
| Channel 3 | +++ | +++ |

Detection of GBS 4.0 μL GBS DNA (1000 copies/μL) was added to Reaction Mixture 1 and to Reaction Mixture 2. Each reaction was performed in triplicate; identical results were obtained for all three reactions in a set. Three 25 μL aliquots of each mixture were divided into three 25 μL I-CORE tubes. Thermocycling was carried out on Smart Cycler® instruments using the following protocol: hold at 95° C. for 3 minutes; then 45 cycles of 95° C., 5 seconds; 60° C. 14 seconds; 72° C. 5 seconds. Real time fluorescence data was collected during the 60° C. annealing step.

The results are presented in the following table. A channel 2 positive signal was detected in both Reaction Mixtures 1 and 2. This result confirmed of presence of the biological agent GBS in the sample. The lack of channel 1 signal in Reaction Mixture 2 confirmed the absence of *B. anthracis*. The lack of channel 1 signal in both reactions confirmed the absence of Bg. A positive signal for channel 3 in both reactions confirmed the presence of IC1 in both reactions and no inhibition of the assay.

| | Cartridge 1 | Cartridge 2 |
|---|---|---|
| Channel 1 | --- | --- |
| Channel 2 | +++ | +++ |
| Channel 3 | +++ | +++ |

Detection of *B. globigii* (Bg)

4.0 µL of *B. globigii* DNA (500 copies/µL) was added to Reaction Mixture 1 and to Reaction Mixture 2. Each reaction was performed in triplicate; identical results were obtained for all three reactions in a set. Three 25 µL aliquots of each mixture were divided into three 25 µL I-CORE tubes. Thermocycling was carried out on Smart Cycler® instruments using the following protocol: hold at 95° C. for 3 minutes; then 45 cycles of 95° C., 5 seconds; 60° C. 14 seconds; 72° C. 5 seconds. Real time fluorescence data was collected during the 60° C. annealing step.

The results are presented in the following table. A channel 1 positive signal was detected in both Reaction Mixtures 1 and 2. This result confirmed of presence of the biological agent Bg in the sample. The lack of channel 2 signal in Reaction Mixture 1 confirmed the absence of Ames in the sample. The lack of channel 2 signal in both reactions confirmed the absence of GBS. A positive signal for channel 3 in both reactions confirmed the presence of IC1 in both reactions and no inhibition of the assay.

| | Cartridge 1 | Cartridge 2 |
|---|---|---|
| Channel 1 | +++ | +++ |
| Channel 2 | --- | --- |
| Channel 3 | +++ | +++ |

Example 2

Identification of Three (3) Different Biological Agents in a Sample Containing More Than One Agent Preparation of Reaction Mixtures Two reaction mixtures are prepared for real time PCR detection of three different organisms: *Bacillus anthracis* Ames strain (Ames); Group B *streptococcus* (GBS); and *Bacillus globigii* (Bg). Each reaction mixture also contains reagents to enable the detection of an internal control (IC1) plasmid and an internal control spore (IC2) as a control for the cell lysis procedure.

Reaction mixtures are prepared as in Example 1.

The following is a tabular representation of the probe labels and cartridge assignments for this experiment, and the expected results (call table):

| | Cartridge 1 | | | | Cartridge 2 | | | |
|---|---|---|---|---|---|---|---|---|
| Agent | Channel 1 | Channel 2 | Channel 3 | Channel 4 | Channel 1 | Channel 2 | Channel 3 | Channel 4 |
| Ames | | Ames gene A | | | Ames gene B | | | |
| GBS | | GBS gene A | | | | GBS gene B | | |
| Bg | Bg gene A | | | | Bg gene B | | | |
| IC1 | | | IC1 | | | | IC1 | |
| IC2 | | | | IC2 | | | | IC2 |

| Agent | Cartridge 1 | Cartridge 2 |
|---|---|---|
| Ames strain | 2 | 1 |
| GBS | 2 | 2 |
| Bg | 1 | 1 |
| IC1 | 3 | 3 |
| IC2 | 4 | 4 |

Detection of Ames Strain and GBS

*B. anthracis* Ames strain spores are sonicated to release DNA and 4.0 μL of 63 cfu/μL are added to Reaction Mixture 1 and to Reaction Mixture 2. Next 4.0 μL GBS DNA (1000 copies/μL) is added to Reaction Mixture 1 and to Reaction Mixture 2. Each reaction is performed in triplicate; identical results are obtained for all three reactions in a set. Three 25 μL aliquots of each mixture are divided into three 25 μL I-CORE tubes. Thermocycling is carried out on Smart Cycler® instruments using the following protocol: hold at 95° C. for 3 minutes; then 45 cycles of 95° C., 5 seconds; 60° C. 14 seconds; 72° C. 5 seconds. Real time fluorescence data is collected during the 60° C. annealing step.

The results are presented in the following table. A channel 2 positive signal is detected in Reaction Mixtures 1 and 2 and a channel 1 positive signal in Reaction Mixture 2. This result confirms the presence of both biological agents *B. anthracis* and GBS in the sample. The lack of channel 1 positive signal in Reaction Mixture 1 confirms the absence of Bg. A positive signal in both channels 3 and 4 in both reactions confirms the presence of IC1 and IC2 in both reactions and no inhibition of the assay.

| | Cartridge 1 | Cartridge 2 |
|---|---|---|
| Channel 1 | --- | +++ |
| Channel 2 | +++ | +++ |
| Channel 3 | +++ | +++ |
| Channel 4 | +++ | +++ |

Detection of GBS and Bg 4.0 μL GBS DNA (1000 copies/μL) and 4.0 μL of *B. globigii* DNA (500 copies/μL) each are added to Reaction Mixture 1 and to Reaction Mixture 2. Each reaction is performed in triplicate; identical results are obtained for all three reactions in a set. Three 25 μL aliquots of each mixture are divided into three 25 μL I-CORE tubes. Thermocycling is carried out on Smart Cycler® instruments using the following protocol: hold at 95° C. for 3 minutes; then 45 cycles of 95° C., 5 seconds; 60° C. 14 seconds; 72° C. 5 seconds. Real time fluorescence data is collected during the 60° C. annealing step.

The results are presented in the following table. A channel 2 positive signal is detected in both Reaction Mixtures 1 and 2. This result confirms of presence of the biological agent GBS in the sample. A channel 1 positive signal is detected in both Reaction Mixtures 1 and 2. This result confirms the presence of the biological agent Bg in the sample. A positive signal in both channels 3 and 4 in both reactions confirms the presence of IC1 and IC2 in both reactions and no inhibition of the assay.

|  | Cartridge 1 | Cartridge 2 |
| --- | --- | --- |
| Channel 1 | +++ | +++ |
| Channel 2 | +++ | +++ |
| Channel 3 | +++ | +++ |
| Channel 4 | +++ | +++ |

Detection of Ames Strain and Bg

*B. anthracis* Ames strain spores are sonicated to release DNA and 4.0 µL of 63 cfu/µL are added to Reaction Mixture 1 and to Reaction Mixture 2. Next, 4.0 µL of *B. globigii* DNA (500 copies/µL) is added to Reaction Mixture 1 and to Reaction Mixture 2. Each reaction is performed in triplicate; identical results are obtained for all three reactions in a set. Three 25 µL aliquots of each mixture are divided into three 25 µL I-CORE tubes. Thermocycling is carried out on Smart Cycler® instruments using the following protocol: hold at 95° C. for 3 minutes; then 45 cycles of 95° C., 5 seconds; 60° C. 14 seconds; 72° C. 5 seconds. Real time fluorescence data is collected during the 60° C. annealing step.

The results are shown in the table below. A channel 2 positive signal is detected in Reaction Mixture 1 and a channel 1 positive signal in Reaction Mixture 2. This result confirms the presence of the biological agent Ames in the sample. An channel 1 positive signal is detected in both Reaction Mixtures 1 and 2. This result confirms the presence of the biological agent Bg in the sample. The lack of channel 2 signal in Reaction Mixture 2 confirms the absence of GBS. A positive signal for both channels 3 and 4 in both reactions confirmed the presence of both IC1 and IC2 in both reactions and no inhibition of the assay.

|  | Cartridge 1 | Cartridge 2 |
| --- | --- | --- |
| Channel 1 | +++ | +++ |
| Channel 2 | +++ | --- |
| Channel 3 | +++ | +++ |
| Channel 4 | +++ | +++ |

While the invention has been particularly shown and described with reference to a preferred embodiment and various alternate embodiments, it will be understood by persons skilled in the relevant art that various changes in form and details can be made therein without departing from the spirit and scope of the invention.

All references, issued patents and patent applications cited within the body of the instant specification are hereby incorporated by reference in their entirety, for all purposes.

What is claimed is:

1. A method for detecting at least first and second biological agents, the first agent comprising first and second markers, and the second agent comprising third and fourth markers, the method comprising:
    (a) preparing first and second mixtures from at least one sample suspected of containing the agents;
    (b) detecting the presence or absence of markers consisting of the first and third markers in the first mixture in a first container; and
    (c) detecting the presence or absence of markers consisting of the second and fourth markers in the second mixture in a second container;
    whereby the presence of the first and second markers indicates the presence of the first biological agent in the sample, and the presence of the third and fourth markers indicates the presence of the second biological agent in the sample.

2. The method of claim 1, wherein the first, second, third and fourth markers are selected from the group consisting of nucleic acids, proteins and polysaccharides.

3. The method of claim 1, wherein:
    the first mixture comprises a first probe specifically recognizing the first marker and a third probe specifically recognizing the third marker:
    the second mixture comprises a second probe specifically recognizing the second marker and a fourth probe specifically recognizing the fourth marker;
    detecting step (b) comprises determining the presence or absence of the first and the third probe binding to the first and the third markers in the first mixture; and
    detecting step (c) comprises determining the presence or absence of the second and the fourth probe binding to the second and the fourth markers in the second mixture.

4. The method of claim 3, wherein the first, second, third or fourth probe is selected from the group consisting of nucleic acids and antibodies.

5. The method of claim 4, wherein at least the first probe is a nucleic acid probe, and at least the fourth probe is an antibody.

6. The method of claim 5, wherein detecting the presence or absence of the first marker comprises PCR amplifying the first marker and hybridizing the first probe to the amplified marker.

7. The method of claim 5, wherein detecting the presence or absence of the fourth marker comprises immunospecifically binding the fourth probe to the fourth marker.

8. The method of claim 3, wherein each of the probes has a detectable label, the detectable label of the first probe is the same as the detectable label of the second probe, and the detectable label of the third probe is different from the detective label of the fourth probe.

9. The method of claim 3, wherein each of the probes has a fluorescent label, the fluorescent label of the first and second probes have respective emission maxima wavelengths within 100 nm of each other, and the fluorescent labels of the third and fourth probes have respective emission maxima wavelengths that differ by more than 100 nm.

10. The method of claim 3, wherein the probes and the markers are nucleic acids and detecting the presence or absence of the markers in the mixtures is performed using PCR.

11. The method of claim 1, wherein the first and second mixtures are prepared from the same sample.

12. The method of claim 1, wherein the first, second, third, and fourth markers comprise first, second, third, and fourth nucleic acid sequences, the first mixture contains hybridization probes for labeling the first and third nucleic acid sequences, and the second mixture contains hybridization probes for labeling the second and fourth nucleic acid sequences.

13. The method of claim 1, wherein at least 3 biological agents are detected in the sample.

14. The method of claim 1, wherein at least 4 biological agents are detected in a sample.

15. A method for optically detecting the presence or absence of a number of biological agents greater than the number of color channels used to detect the presence or absence of the biological agents, each of the biological agents having respective first and second nucleic acid sequences that differentiate the biological agent from the other biological agents, the method comprising the steps of:
 a) forming first and second mixtures in first and second containers, respectively, from at least one sample suspected of containing the biological agents, wherein:
  i) the first mixture comprises reagents and probes, wherein said probes consist essentially of, for each of the biological agents, a respective first probe set for labeling the first nucleic acid sequence of the biological agent;
  ii) the second mixture comprises reagents and probes, wherein said probes consist essentially of, for each of the biological agents, a respective second probe set for labeling the second nucleic acid sequence of the biological agent;
  iii) at least two of the first probe sets in the first mixture have the same emission wavelength ranges to be detected in the same color channel, and the at least two corresponding second probe sets in the second mixture have different emission wavelength ranges to be detected in different color channels;
 b) optically reading the presence or absence of probe signals from the at least two of the first probe sets in the first mixture have the same emission wavelength ranges;
 c) optically reading the presence or absence of probe signals from the at least two corresponding second probe sets in the second mixture have different emission wavelength ranges; and
 d) determining from the combination of probe signals received from each of the mixtures the presence or absence of the biological agents.

16. A method for detecting at least first and second biological agents, the first agent comprising first and second markers, and the second agent comprising third and fourth markers, the method comprising:
 a) preparing a first mixture in a first container from at least one sample suspected of containing the agents;
 b) detecting the presence or absence of markers consisting of the first and third markers in the first container;
 c) if either of the first or third markers is present in the first container, preparing a second mixture in a second container from the at least one sample; and
 d) detecting the presence or absence of markers consisting of the second and fourth markers in the second container;
  whereby the presence of the first and second markers indicates the presence of the first biological agent in the sample, and the presence of the third and fourth markers indicates the presence of the second biological agent in the sample.

17. The method of claim 16, wherein the first, second, third, and fourth markers comprise first, second, third, and fourth nucleic acid sequences, the first mixture contains reagents and probes for amplifying and detecting the first and the third nucleic acid sequences, and the step of detecting the presence or absence of the first and third markers in the first container comprises subjecting the first mixture to nucleic acid amplification conditions and determining from probe signals if either of the first or third nucleic acid sequences is present in the first mixture.

18. The method of claim 17, wherein the second mixture contains reagents and probes for amplifying and detecting the second and the fourth nucleic acid sequences, and the step of detecting the presence or absence of the second and fourth markers in the second container comprises subjecting the second mixture to nucleic acid amplification conditions and determining from probe signals if either of the second or fourth nucleic acid sequences is present in the second mixture.

19. A kit for detecting at least first and second biological agents, the first agent comprising first and second markers, and the second agent comprising third and fourth markers, the kit comprising at least first and second containers, wherein the first container houses reagents and a first probe set consisting essentially of a first probe specifically recognizing the first marker and a second probe specifically recognizing the third marker, and wherein the second container houses reagents and a second probe set consisting essentially of a third probe specifically recognizing the second marker and a fourth probe specifically recognizing the fourth marker.

20. The kit of claim 19, wherein the first, second, third and fourth markers are selected from the group consisting of nucleic acids, proteins and polysaccharides.

21. The kit of claim 19, wherein the first, second, third or fourth probe is selected from the group consisting of nucleic acids and antibodies.

22. The kit of claim 19, wherein each of the probes has a detectable label, the detectable label of the first probe is the same as the detectable label of the third probe, and the detectable label of the second probe is different from the detective label of the fourth probe.

23. The kit of claim 19, wherein each of the probes has a fluorescent label, and wherein the fluorescent label of the first and second probes have respective absorbance maxima wavelengths within 100 nm of each other.

24. The kit of claim 19, wherein each of the probes has a fluorescent label, the fluorescent labels of the first and second probes have respective emission maxima wavelengths within 100 nm of each other, and the third and fourth probes have respective emission maxima wavelengths that differ by more than 100 nm.

25. The kit of claim 19, wherein at least the first probe is a nucleic acid probe, and at least the fourth probe is an antibody.

26. The kit of claim 19, wherein the first, second, third, and fourth markers comprise first, second, third, and fourth nucleic acid sequences, respectively, and wherein the probes comprise hybridization probes for labeling the nucleic acid sequences.

27. The kit of claim 26, wherein the first container further contains primers for amplifying the first and third nucleic acid sequences, and wherein the second container further contains primers for amplifying the second and fourth nucleic acid sequences.

28. The kit of claim 19, wherein the first, second, third, and fourth markers comprise first, second, third, and fourth nucleic acid sequences, respectively, the first container further contains amplification reagents for amplifying the first and third nucleic acid sequences, and wherein the second container further contains amplification reagents for amplifying the second and fourth nucleic acid sequences.

29. A system for detecting at least first and second biological agents, wherein the first agent comprises first and second markers, and the second agent comprises third and fourth markers, the system comprising:
  (a) at least first and second containers, the first container housing reagents and probes for detecting markers consisting of the first and third markers and the second container housing reagents and probes for detecting markers consisting of the second and fourth markers;
  (b) at least one detector arranged to detect the presence or absence of the markers in the containers; and
  (c) at least one controller in communication with the at least one detector, the controller being programmed with computer-readable instructions to perform a series of operations comprising:
    i) initiating a detection reaction in the first container;
    ii) receiving data from the detector; and
    iii) determining from the data the presence or absence of the first and third markers in the first container;
    wherein if the first or third markers is present in the first container, the controller performs a second series of operations comprising;
    iv) initiating a second detection reaction in the second container;
    v) receiving additional data from the detector; and
    vi) determining from the additional data the presence or absence of the second or fourth markers in the second container;
    whereby the presence of the first and second markers indicates the presence of the first biological agent in a sample, and the presence of the third and fourth markers indicates the presence of the second biological agent in the sample.

30. The system of claim 29, wherein the markers are nucleic acids, the reagents housed in the first container are nucleic acid probes specifically recognizing the first and the third markers, and the reagents housed in the second container are nucleic acid probes specifically recognizing the second and the fourth markers.

31. The system of claim 30, wherein the detection reaction comprises nucleic acid amplification.

32. The system of claim 29, wherein the system comprises at least first and second detectors in communication with the controller, the first detector being arranged to detect the presence or absence of one or more of the markers in the first container, and the second detector being arranged to detect the presence or absence of one or more of the markers in the second container.

33. The system of claim 29, wherein the first, second, third, and fourth markers comprise first, second, third, and fourth nucleic acid sequences, and wherein the first and second containers comprise cartridges for extracting nucleic acid from a sample and for holding the nucleic acid for detection.

34. An automated system for determining the presence or absence of a plurality of agents, each of the agents comprising respective first and second nucleic acid sequences that differentiate the agent from the other agents, the automated system comprising:
  a) at least one temperature control system for subjecting first and second reaction mixtures suspected of containing the agents to nucleic acid amplification conditions, the first reaction mixture consisting essentially of reagents and probes for amplifying and detecting the first nucleic acid sequence of each of the agents, and the second reaction mixture consisting essentially of reagents and probes for amplifying and detecting the second nucleic acid sequence of each of the agents;
  b) at least one detection mechanism arranged to detect probe signals from the reaction mixtures; and
  c) at least one controller in communication with the at least one temperature control system and with the at least one detection mechanism, the controller being programmed to perform the steps of:
    i) sending control signals to the temperature control system to subject the first reaction mixture to nucleic acid amplification conditions;
    ii) determining from probe signals received from the first reaction mixture if the first nucleic acid sequence of any of the agents is present in the first reaction mixture;
    iii) if the first nucleic acid sequence of any of the agents is present in the first reaction mixture, then sending control signals to the temperature control system to subject the second reaction mixture to nucleic acid amplification conditions; and
    iv) determining from probe signals received from the second reaction mixture if the second nucleic acid sequence of any of the agents is present in the second reaction mixture;
    whereby the presence of the first and the second nucleic acid sequences of any of the agents is indicative of the presence of that agent.

35. The system of claim 34, wherein the system comprises at least first and second detection mechanisms in communication with the controller, the first detection mechanism being arranged to detect the presence or absence of one or more of the nucleic acid sequences in the first reaction mixture, and the second detection mechanism being arranged to detect the presence or absence of one or more of the nucleic acid sequences in the second reaction mixture.

* * * * *